(12) United States Patent
Takahashi

(10) Patent No.: US 9,164,005 B2
(45) Date of Patent: Oct. 20, 2015

(54) DYNAMOMETER SYSTEM

(71) Applicant: MEIDENSHA CORPORATION, Tokyo (JP)

(72) Inventor: Toshimichi Takahashi, Tokyo (JP)

(73) Assignee: MEIDENSHA CORPORATION, Tokyo (JP)

( * ) Notice: Subject to any disclaimer, the term of this patent is extended or adjusted under 35 U.S.C. 154(b) by 0 days.

(21) Appl. No.: 14/381,457

(22) PCT Filed: Feb. 27, 2013

(86) PCT No.: PCT/JP2013/055254
§ 371 (c)(1),
(2) Date: Aug. 27, 2014

(87) PCT Pub. No.: WO2013/129532
PCT Pub. Date: Sep. 6, 2013

(65) Prior Publication Data
US 2015/0101421 A1   Apr. 16, 2015

(30) Foreign Application Priority Data

Feb. 29, 2012  (JP) .................................. 2012-043215

(51) Int. Cl.
*G01L 3/02* (2006.01)
*G01L 3/04* (2006.01)
(Continued)

(52) U.S. Cl.
CPC ............... *G01L 3/045* (2013.01); *G01L 5/0042* (2013.01); *H02P 6/06* (2013.01); *H02P 23/12* (2013.01); *G01N 2203/021* (2013.01)

(58) Field of Classification Search
CPC ......... G01L 3/045; G01L 3/10; G01L 5/0042; G01L 5/24; G01N 2203/021; H02P 23/12

USPC .............................. 73/862, 862.325, 862.193
See application file for complete search history.

(56) References Cited

U.S. PATENT DOCUMENTS 5,063,773 A * 11/1991 Fujimori et al. ........... 73/116.06
5,385,042 A * 1/1995 La Belle .................... 73/116.06
(Continued)

FOREIGN PATENT DOCUMENTS

JP   05-100709   4/1993
JP   08-190402   7/1996
(Continued)

*Primary Examiner* — Max Noori
(74) *Attorney, Agent, or Firm* — Muncy, Geissler, Olds & Lowe, P.C.

(57) ABSTRACT

Provided is a dynamometer system capable of stable speed control and position control even in instances of large load inertia. A speed-control device (6C) in a dynamometer system is provided with: a speed-control-circuit unit (61A) for calculating a torque-current-command value (T2) on the basis of an angular-velocity-command value ($\omega$ref) and the angular velocity ($\omega$M) of the dynamometer; a disturbance-observer-compensation unit (63C) for correcting the torque-current-command value by subtracting a disturbance observer (Tobs) from the torque-current-command value (T2); and a shaft-torque-detection-compensation unit (62A) for correcting the torque-current-command value by adding a shaft-torque-detection-compensation amount (Tsh_K), which is obtained by multiplying a filter transfer function ($G_{BPF}$) and a control gain (K1) by a shaft-torque-detection value (Tsh), to a torque-current-command value (T1). Therein, the filter transfer function ($G_{BPF}$) has only the resonance frequency and vicinity thereof for mechanical systems comprising load devices and dynamometers set as a passband.

7 Claims, 10 Drawing Sheets

(51) Int. Cl.
*H02P 6/06* (2006.01)
*H02P 23/12* (2006.01)
*G01L 5/00* (2006.01)

(56) References Cited

U.S. PATENT DOCUMENTS

| | | |
|---|---|---|
| 5,729,111 A | 3/1998 | Ogura et al. |
| 2013/0339892 A1* | 12/2013 | Watanabe et al. ............. 715/771 |
| 2015/0039246 A1* | 2/2015 | Takahashi ...................... 702/41 |

FOREIGN PATENT DOCUMENTS

| | | |
|---|---|---|
| JP | 09-121580 | 5/1997 |
| JP | 2007-252142 | 9/2007 |
| JP | 2009-289369 | 12/2009 |
| JP | 2011-36061 A | 2/2011 |
| JP | 2011-152005 | 8/2011 |
| JP | 2011-257205 | 12/2011 |

* cited by examiner

DYNAMOMETER SYSTEM

TECHNICAL FIELD

The present invention relates to a dynamometer system. In more detail, it relates to a dynamometer system including an encoder that detects a rotational position or angular velocity of a dynamometer, and a shaft torque meter that detects the shaft torque between a load device and the dynamometer, and controlling the dynamometer based on the detection values of these.

BACKGROUND ART

With a dynamometer system, by connecting a load device such as an electric motor, engine and roller with a dynamometer that absorbs the dynamic force generated by this load device, as well as controlling the velocity or position of the dynamometer based on the detection signals of an encoder and shaft torque meter, and controlling the output of the load device while applying an appropriate load to the load device, various performance tests thereof are carried out.

As the speed-control device of such a dynamometer (electric motor), for example, Patent Document 1 has become well-known. More specifically, the speed-control device of Patent Document 1 is configured by a 2-degree-of-freedom control system in which feed-forward compensation is added to I-P speed control in order to achieve both response to command values and response to disturbances. In particular, a method of uniquely setting a plurality of control parameters such as proportional gain and integral gain in such a 2-degree-of-freedom control system is shown in Patent Document 1.

[Patent Document 1] Japanese Unexamined Patent Application, Publication No. 2011-152005

DISCLOSURE OF THE INVENTION

Problems to be Solved by the Invention

According to the speed-control device of Patent Document 1, speed control which facilitates adjustment of control parameters while having little steady-state deviation becomes possible; however, the inertia of the load connected to the dynamometer is nevertheless not sufficiently considered. For this reason, in the case of applying the speed-control device of Patent Document 1 as is to the above-mentioned dynamometer system, if raising the control response, for example, there is a risk of instability phenomena such as hatching and divergence arising, caused by the resonance characteristics of the mechanical system configured by the dynamometer and load device, and thus stable speed control becomes difficult. In particular, the tendency thereof becomes remarkable with greater inertia moment of the load device.

The present invention has been made taking account of the above such problems, and has an object of providing a dynamometer system that enables stable speed control or position control even if the inertia of the load is great.

Means for Solving the Problems

In order to achieve the above-mentioned object, a first aspect of the present invention provides a dynamometer system (e.g., the dynamometer system 1 described later) includes: a dynamometer (e.g., the dynamometer 2 described later) that is connected by a common shaft (e.g., the shaft S described later) to a load device (e.g., the electric motor 9 described later); an inverter (e.g., the inverter 3 described later) that supplies electric power to the dynamometer; an encoder (e.g., the encoder 4 described later) that detects a rotational position or angular velocity of the dynamometer; a shaft torque meter (e.g., the shaft torque meter 5 described later) that detects shaft torque between the load device and the dynamometer; and a control device (e.g., the speed-control device 6, 6A, 6A', 6B, 6B', 6C, 6D or position control device described later) that controls the dynamometer based on a detection value of the encoder and a detection value of the shaft torque meter. The control device includes: a main control unit (e.g., the speed-control-circuit 61A described later) that calculates a torque-current-command value (T1, T2) to serve as an input (Tdyref) to the inverter, based on a command value ($\omega$ref) with respect to the detection value ($\omega$m) of the encoder inputted externally, and the detection value ($\omega$M) of the encoder; and a shaft-torque-detection-compensation unit (e.g., the shaft-torque-detection-compensation unit 62A, 62A', 62B, 62B' described later) that adds a value arrived at by multiplying a filter transfer function ($G_{BPF}$, $G_{LPF} \cdot G_{HPF}$) and a suppression gain (K1) by the detection value of the shaft torque meter, to the torque-current-command value (T1, T2) calculated by the main control unit, so as to correct the torque-current-command value;s and the filter transfer function of the shaft-torque-detection-compensation unit is set with only a resonance frequency of a mechanical system consisting of the load device and the dynamometer and a vicinity thereof as a passband.

According to the first aspect of the present invention, by correcting the torque-current-command value calculated by the main control unit based on the detection value of the encoder and the command value thereof, by way of the shaft-torque-detection-compensation unit, with a value arrived at by multiplying the suppression gain by the detection value of the shaft torque meter, the resonance gain of the mechanical system consisting of the load device and dynamometer is suppressed, and thus stable speed control or positional control of the dynamometer becomes possible.

However, when taking account of the noise of the shaft torque meter, appropriate correction over the entire frequency domain becomes difficult with only the above-mentioned shaft-torque-detection-compensation unit using the detection value of the shaft torque meter, and cases in which combining with another compensator is more preferable are also assumed. Therefore, in the present invention, the shaft-torque-detection-compensation unit multiplies the filter transfer function, which is set with only the resonance frequency of the mechanical system consisting of the load device and the dynamometer and the vicinity thereof as the passband, by the detection value of the shaft torque meter. In other words, by configuring to compensate only the resonance frequency band of the mechanical system, in the case of using in combination with another compensator, the shaft-torque-detection-compensation unit suppresses the interference with this, a result of which stable speed control or position control becomes possible over the entire frequency domain.

According to a second aspect, in this case, it is preferable for the dynamometer system to further include: a disturbance observer compensation unit (e.g., the disturbance observer compensation unit 63C described later) that calculates a disturbance observer (Tobs) based on the detection value ($\omega$M) of the encoder and the torque-current-command value (T1) calculated by the main control unit, and subtracts the disturbance observer thus calculated from the torque-current-command value (T2) calculated by the main control unit, so as to correct the torque-current-command value.

According to the second aspect of the present invention, the disturbance observer compensation unit is further provided, and by correcting the torque-current-command value calculated by the main control unit with the disturbance observer calculated based on the detection value of the encoder and torque-current-command value, the disturbance response improves, whereby more highly-responsive speed control or position control of the dynamometer becomes possible. In addition, with the present invention, by combining the disturbance observer compensation unit to use with the shaft-torque-detection-compensation unit set so as to compensate only the resonance frequency band as mentioned above, both are made to cooperate, whereby highly-responsive and stable speed control or position control over the entire frequency domain becomes possible.

According to a third aspect, in this case, it is preferable for the disturbance observer compensation unit to calculate a disturbance observer Tobs by way of formula (1) below, in which J is an overall inertia moment combining the dynamometer and the load device, ωM is the detection value of the encoder, T1 is the torque-current-command value calculated by the main control unit, s is a Laplace operator, 1/Gfc(s) is any transfer function having a relative degree of at least one dimension and having a characteristic of blocking a frequency band higher than a predetermined cut-off frequency.

$$Tobs = \frac{(J \cdot \omega M \cdot s) - T1}{Gfc(s)} \quad (1)$$

According to the third aspect of the present invention, by calculating the disturbance observer as an estimated value of disturbance by an inverse model taking consideration of the overall inertia moment combining the load device and dynamometer as in formula (1) above, and correcting the torque-current-command value with this, the disturbance response is improved, and more highly-responsive speed control or position control of the dynamometer becomes possible. In addition, when the response on the high frequency side becomes difficult due to the influence of noise since a pseudo differential of the detection value of the encoder is included in the estimated value of disturbance serving as the disturbance observer, it is possible to eliminate the influence of such noise by multiplying the transfer function 1/Gfc (s) having the above-mentioned such low-pass characteristic.

According to a fourth aspect, in this case, it is preferable for the cut-off frequency of the transfer function 1/Gfc(s) to be set to be lower than the resonance frequency.

According to the fourth aspect of the present invention, by making the cut-off frequency lower than the resonance frequency of the mechanical system as described above, it is configured so as to compensate with the disturbance observer compensation unit on the low frequency side, and compensate with the shaft-torque-detection-compensation unit on the high frequency side, whereby highly-responsive and stable speed control or position control over the entire frequency domain becomes possible by making both cooperate.

According to a fifth aspect, in this case, it is preferable for the filter transfer function of the shaft-torque-detection-compensation unit to be a band-pass filter set so that the resonance frequency of the mechanical system is included in the bandwidth between a upper cut-off frequency and lower cut-off frequency thereof.

According to the fifth aspect, by configuring the filter transfer function to be a band-pass filter set so that the resonance frequency is included in the bandwidth thereof, it is possible to more reliably exert the effects of the above-mentioned first aspect.

According to a sixth aspect, in this case, it is preferable for the filter transfer function of the shaft-torque-detection-compensation unit to be configured by connecting a high-pass filter having a cut-off frequency lower than the resonance frequency in series to a low-pass filter having a cut-off frequency higher than the resonance frequency.

According to the sixth aspect of the present invention, it is possible to exert the same effects as the above-mentioned fifth aspect by connecting in parallel a low-pass filter and a high-pass filter to configure a filter transfer function having a characteristic of a band-pass filter. It should be noted that, since a filter made by combining a low-pass filter and a high-pass filter can establish a wider bandwidth compared to a band-pass filter, it is possible to raise the degree of freedom in design of the shaft-torque-detection-compensation unit when comparing with the invention of the above-mentioned fifth aspect.

According to a seventh aspect, in this case, it is preferable for the shaft-torque-detection-compensation unit to be configured by joining in parallel a plurality of filter transfer functions set for each of the resonance frequencies and a suppression gain thereof, for a plurality of resonance frequencies of the mechanical system.

According to the seventh aspect, since a plurality of resonance frequencies generally exist, with the present invention, by joining the filter transfer functions set for each of the respective resonance frequencies and the suppression gains thereof in parallel, each resonance gain can be suitably suppressed.

Figure 1:
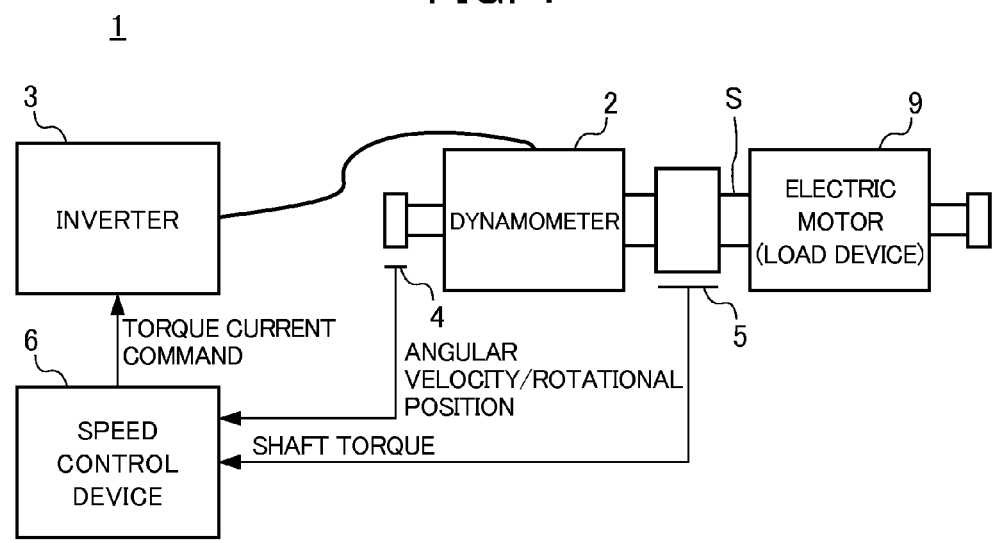
FIG. 1 is a block diagram showing the configuration of a dynamometer system according to an embodiment of the present invention.

EXPLANATION OF REFERENCE NUMERALS 1 dynamometer system
2 dynamometer
3 inverter
4 encoder
5 shaft torque meter

6, 6A, 6A', 6B, 6B', 6C, 6D speed-control device (control device)
 61A speed-control-circuit (main control unit)
 62A, 62A', 62B, 62B' shaft-torque-detection-compensation unit
 63C disturbance observer compensation unit.

PREFERRED MODE FOR CARRYING OUT THE INVENTION

Hereinafter, a dynamometer system according to an embodiment of the present invention will be explained in detail while referencing the drawings.

FIG. 1 is a block diagram showing the configuration of dynamometer system 1 of the present embodiment.

The dynamometer system 1 includes: a dynamometer 2 connected with a common shaft S with an electric motor 9 as a load device; an inverter 3 that supplies electric power to this dynamometer 2; an encoder 4 that detects the rotational position or angular velocity of the dynamometer 2; a shaft torque meter 5 that detects the shaft torque between the electric motor 9 and the dynamometer 2; and a speed-control device 6 that controls the angular velocity of the dynamometer 2 based on the detection values of this encoder 4 and shaft torque meter 5.

The encoder 4 detects the rotational position or angular velocity of the dynamometer 2, and sends a signal substantially proportional to the detection signal to the velocity control device 6. The shaft torque meter 5 detects shaft torque acting on the shaft S between the electric motor 9 and dynamometer 2 from the amount of deformation in a twisting direction of the shaft, for example, and sends a signal substantially proportion to the detection value to the speed-control device 6.

The inverter 3 converts direct-current power supplied from a direct-current power source that is not illustrated, into alternating-current power, and then supplies to the electric motor 1. The speed-control device 6 determines a torque-current-command value that is an input to the inverter 3, based on the detection value of the encoder 4, the detection value of the shaft torque meter 5, and the angular-velocity-command value input externally. The detailed configuration of this speed-control device 6 will be explained in each of the examples later.

With the dynamometer system 1, by controlling the angular velocity of the dynamometer 2 with the above-mentioned speed-control device 6 and controlling the output of the electric motor 9 while applying an appropriate load to the electric motor 9, various performance tests thereof are carried out.

EXAMPLE 1

Next, Example 1 of the speed-control device of the above-mentioned embodiment will be explained in detail while referencing the drawings. In the following explanation of the Examples, the configuration of the mechanical system of the dynamometer system is defined as a 2-inertia system model like that shown in FIG. 2

Figure 2:
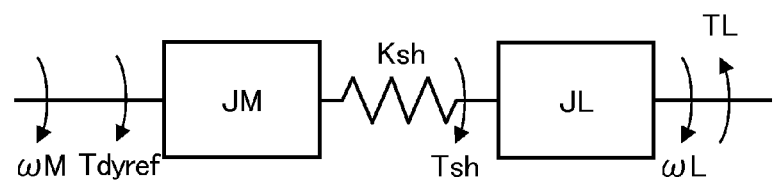
FIG. 2 is a diagram showing the configuration of 2-inertia system model.

In FIG. 2, "JM" is the inertia moment (kgm$^2$) of the dynamometer.

"JL" is the inertia moment (kgm$^2$) of the electric motor (load device).

"Ksh" is the spring stiffness (Nm/rad) of the shaft between the dynamometer and electric motor.

"ωm" is the angular velocity (rad/s) of the dynamometer, and corresponds to the detection value of the encoder. Hereinafter, it is referred to as dynamometer angular velocity.

"ωL" is the angular velocity (rad/s) of the electric motor.

"TL" is the drive torque (Nm) of the electric motor.

"Tsh" is the shaft torque (Nm) acting on the shaft between the dynamometer and electric motor, and corresponds to the detection value of the shaft torque meter. Hereinafter, it is referred to as shaft torque meter detection value.

"Tdyref" is the drive torque (Nm) of the dynamometer, and corresponds to the input to the inverter. Hereinafter, it is referred to as torque-current-command value.

In the following explanation, although the rotating loss (Nms/rad) or spring loss (Nms/rad) are omitted from explanation, the present invention is not limited thereto.

In the case of trying to raise the speed control response in a 2-inertia system model like that shown in FIG. 2, when the inertia moment JL of the load becomes greater than the inertia moment JM of the dynamometer (JL≥JM), instability phenomena such as hatching and divergence tend to occur due to the resonance of the mechanical system. Hereinafter, the configuration of a speed-control device configured to suppress such resonance will be explained.

Figure 3:
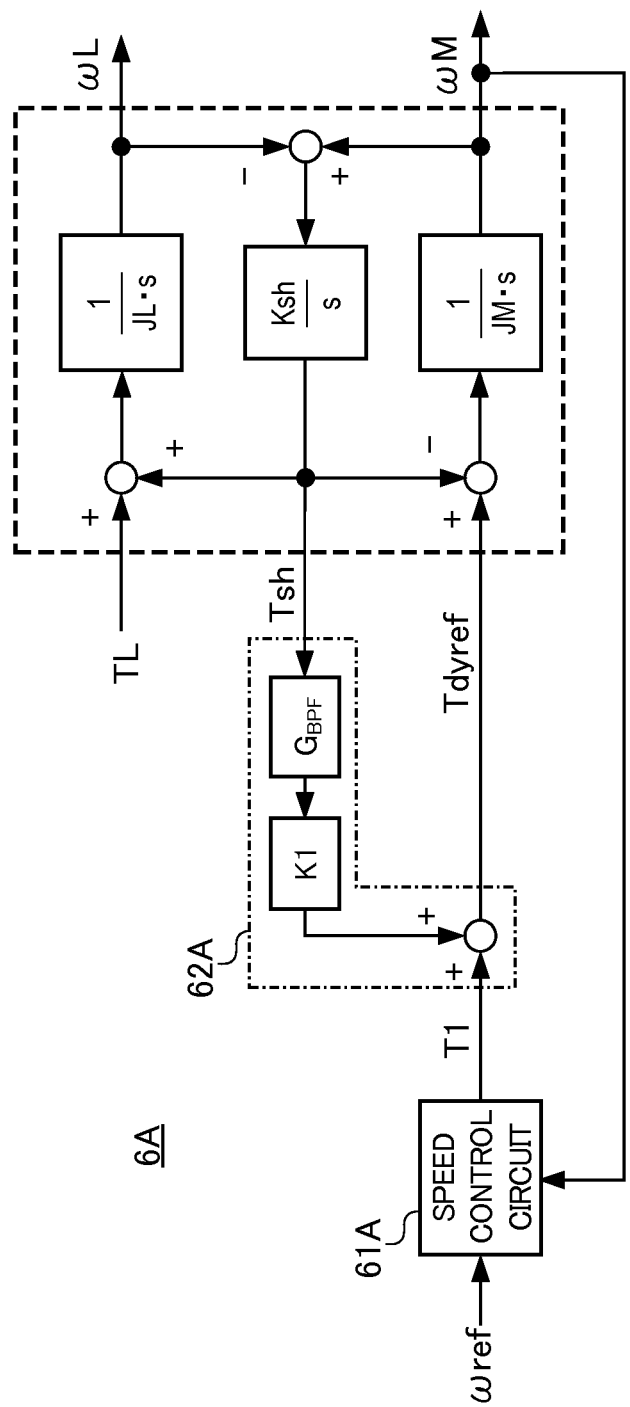
FIG. 3 is a block diagram showing the entirety of a control system of Example 1.

FIG. 3 is a block diagram showing the entirety of a control system to which a speed-control device 6A of the present example is applied. It should be noted that the portion indicated by the bold dotted-line in FIG. 2 is a portion in which the 2-inertia system model explained referencing FIG. 2 is represented by a transfer function.

In the control system shown in FIG. 3, the manipulated variable is the drive torque Tdyref of the dynamometer, the observables are the dynamometer angular velocity ωM and the shaft torque meter detection value Tsh, and the controlled variable is the dynamometer angular velocity ωM, and it is configured so that the drive torque TL is added to the electric motor side as a disturbance.

The speed-control device 6A of Example 1 is configured to include a speed-control-circuit 61A and a shaft-torque-detection-compensation unit 62A. As a command value to the dynamometer angular velocity ωM, an angular-velocity-command value ωref (rad/s) is input externally to the speed-control device 6A.

The speed-control-circuit 61A calculates a torque-current-command value T1 serving as an input to the inverter, based on the angular-velocity-command value ωref inputted externally and the dynamometer angular velocity detection value ωM, so that the deviation of these quickly becomes 0. A conventionally known circuit is used as this speed-control-circuit 61A.

The shaft-torque-detection-compensation unit 62A calculates a shaft-torque-detection-compensation amount Tsh_K by multiplying a filter transfer function $G_{BPF}$ and suppression gain K1 by the shaft torque meter detection value Tsh, and adds this to the torque-current-command value T1 calculated by the speed-control-circuit 61A, so as to correct the torque-current-command value T1.

In the present example, a value arrived at by adding the shaft-torque-detection-compensation amount Tsh_K calculated by the shaft-torque-detection-compensation unit 62A to the torque-current-command value T1 calculated by the speed-control-circuit 61A becomes the final torque-current-command value Tdyref.

The suppression gain K1 is adjusted between a value greater than 0 and a value smaller than 1. For the filter transfer function $G_{BPF}(s)$, a band-pass filter like that represented by formula (2) below is used. In formula (2) below, Bω1 is the center frequency (rad/s). Pg1 is the peak gain. BQ1 is the Q value, and when ±3 dB width (bandwidth) from the center frequency Bω1 is set as Bwidth1, the Q value BQ1 is represented by Bω1/Bwidth1.

$$G_{BPF} = \frac{\frac{B\omega 1}{BQ1} \cdot s}{s^2 + Pg1 \cdot \frac{B\omega 1}{BQ1} \cdot s + B\omega 1^2} \quad (2)$$

Herein, in the filter transfer function $G_{BPF}(s)$ shown in formula (2) above, the peak gain Pg1 is set to 1, for example, and the center frequency $B\omega 1$ and bandwidth Bwidth1 are set so that the resonance frequency of the mechanical system is included in the bandwidth Bwidth1.

Figure 4:
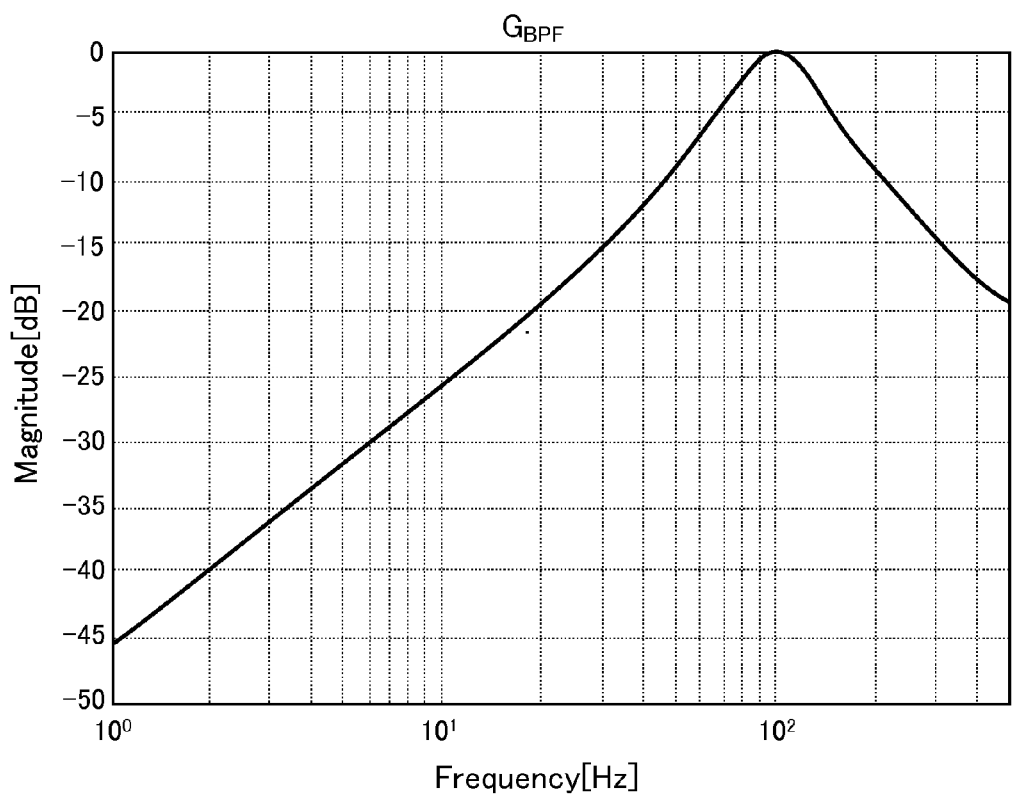
FIG. 4 is a graph showing the frequency characteristics of a filter transfer function $G_{BPF}$ of Example 1.

FIG. 4 is a graph showing the frequency characteristics of the filter transfer function $B_{BPF}$. FIG. 4 shows an example of the filter transfer function $G_{BPF}$ set under the assumption that there is a resonance point of the mechanical system in the vicinity of 100 Hz (refer to FIG. 10 described later). In this way, the filter transfer function $G_{BPF}$ of the shaft-torque-detection-compensation unit 62A set with only this resonance frequency and the vicinity thereof as the passband, in accordance with the resonance frequency of the mechanical system provided in advance.

The following effects are exerted according to the present example.

(1) By correcting the torque-current-command value T1 calculated by the speed-control-circuit 61A based on the dynamometer angular velocity $\omega M$ and the command value thereof $\omega ref$, by way of the shaft-torque-detection-compensation unit 62A, the resonance gain of the mechanical system is suppressed, and thus stable speed control of the dynamometer becomes possible. In addition, with the shaft-torque-detection-compensation unit 62A, the filter transfer function $G_{BPF}$ set with only the resonance frequency of the mechanical system and the vicinity thereof as the passband is multiplied by the shaft torque meter detection value Tsh. In other words, with the shaft-torque-detection-compensation unit 62A, by configuring to compensate only the resonance frequency band of the mechanical system, in the case of using in combination with another compensator such as the disturbance observer compensation unit described later, the interference with this is suppressed, and stable speed control becomes possible over the entire frequency range as a result.

MODIFIED EXAMPLE OF EXAMPLE 1

Next, a modified example of Example 1 will be explained in detail by referencing the drawings.

Figure 5:
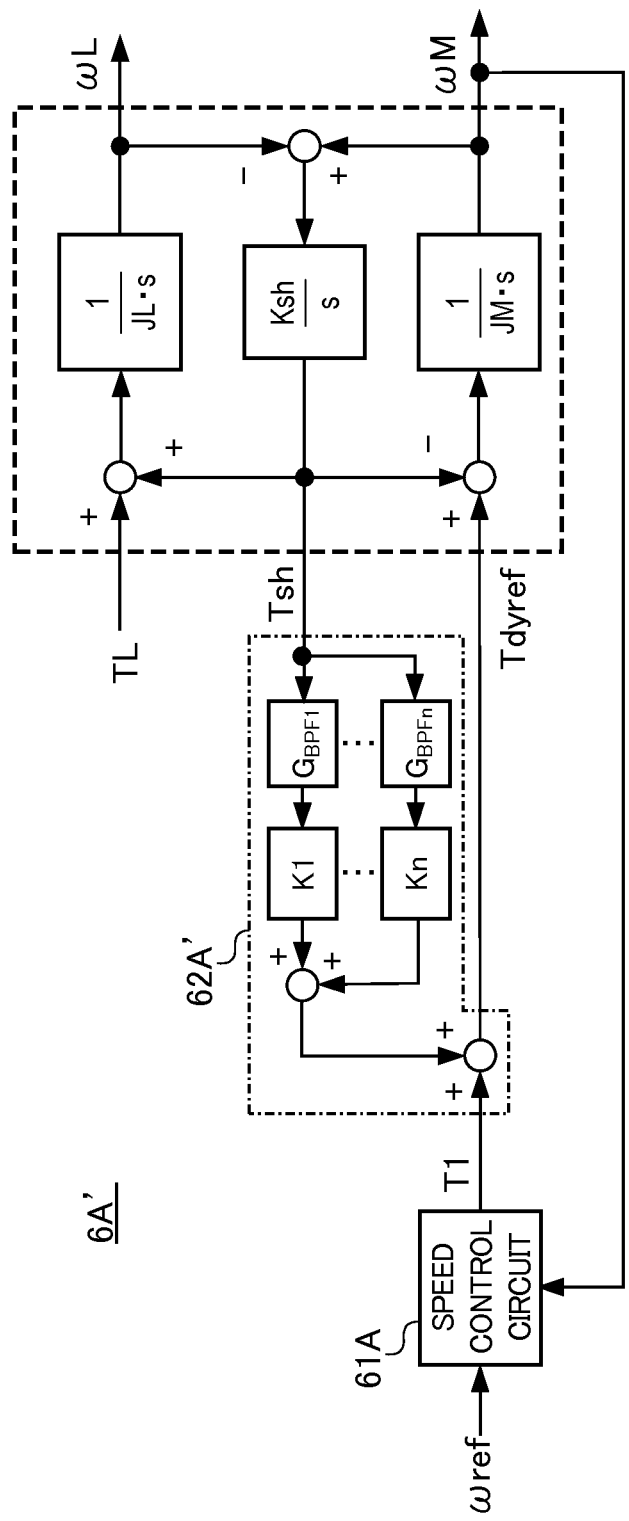
FIG. 5 is a block diagram showing the entirety of a control system of a modified example of Example 1.

FIG. 5 is a block diagram showing the entirety of a control system to which the speed control device 6A' of the present modified example is applied. The configuration of the shaft-torque-detection-compensation unit 62A' differs comparing with the above Example 1 shown in FIG. 3.

Although simplified to the 2-inertia system model in the above-mentioned example, generally, a plurality of resonance points exist. The shaft-torque-detection-compensation unit 62A' of the present modified example assumes that a plurality of resonance points exist, and is configured by joining a plurality of filter transfer functions $G_{BPFn}$ and suppression gains Kn set for each of the resonance frequencies in parallel. More specifically, the shaft-torque-detection-compensation unit 62A' sets filter transfer functions $G_{BPFn}$ and suppression gains Kn in the aforementioned way for each of the resonance frequencies, and establishes a value summing all of the compensation amounts Tsh_Kn obtained by multiplying the shaft torque meter detection value Tsh by each of the filter transfer functions $G_{BPFn}$ and suppression gains Kn, as the shaft-torque-detection-compensation amount Tsh_K.

The $n^{th}$ suppression gain Kn corresponding to an $n^{th}$ resonance point is set between a value greater than 0 and a value less than 1, and for the $n^{th}$ filter transfer function a bandpass filter is used that is characterized by a center frequency $B\omega n$, peak gain Pgn, Q value BQn (=$B\omega n$/Bwidthn) and bandwidth Bwidthn, like that of formula (3) below. The center frequency $B\omega n$ and bandwidth Bwidthn are set so that the corresponding resonance frequency is included in the bandwidth Bwidthn, as mentioned above.

$$G_{BPFn} = \frac{\frac{B\omega n}{BQn} \cdot s}{s^2 + Pgn \cdot \frac{B\omega n}{BQn} \cdot s + B\omega n^2} \quad (3)$$

In addition to the effect of above-mentioned (1), there is the following effect according to the present modified example.

(2) By joining the filter transfer function $G_{BPFn}$ set for each resonance frequency and the suppression gain Kn thereof in parallel, each resonance gain can be suitably suppressed.

EXAMPLE 2

Next, Example 2 of a speed-control device of the above-mentioned embodiment will be explained while referencing the drawings.

Figure 6:
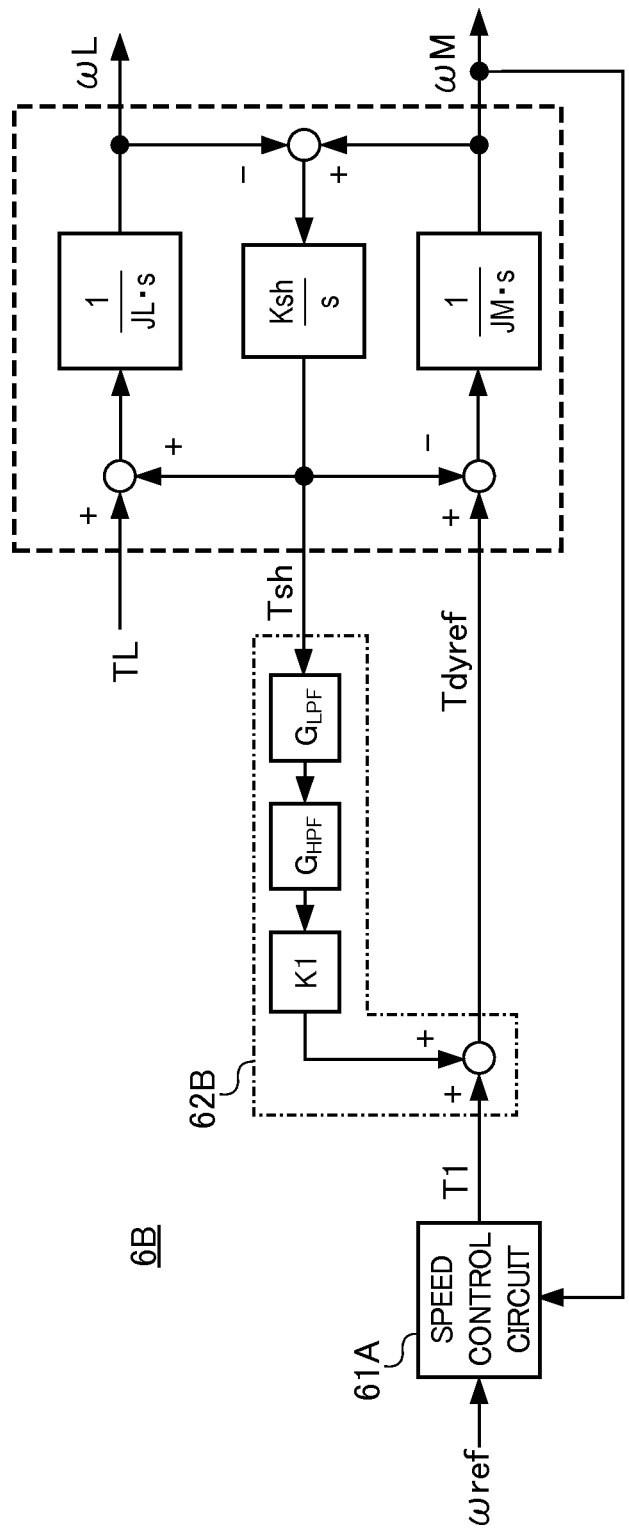
FIG. 6 is a block diagram showing the entirety of a control system of Example 2.

FIG. 6 is a block diagram showing an entirety of a control system to which a speed-control device 6B of the present example is applied. It should be noted that, for the speed-control device 6B of the present example, the configuration of the shaft-torque-detection-compensation unit 62B differs compared to the above-mentioned Example 1.

The shaft-torque-detection-compensation unit 62B calculates the shaft-torque-detection-compensation amount Tsh_K by multiplying the filter transfer functions $G_{LFP}(s)$ and $G_{HPF}(s)$ and suppression gain K1 by the shaft torque meter detection value Tsh, and adds this to the torque-current-command value T1 calculated by the speed-control-circuit 61A so as to correct the torque-current-command value T1.

The suppression gain K1 is adjusted between a value greater than 0 and a value less than 1. For the filter transfer function $G_{LFP}(s)$ and filter transfer function $G_{HPF}(s)$, a low-pass filter characterized by the cut-off frequency LPF$\omega c$ and a high-pass filter characterized by the cut-off frequency HPF$\omega c$ are respectively used, as shown in formula (4) below, for example.

$$G_{LPF} = \frac{1}{1 + \frac{1}{LPF\omega c} \cdot s},$$

$$G_{HPF} = \frac{\frac{1}{HPF\omega c} \cdot s}{1 + \frac{1}{HPF\omega c} \cdot s} \quad (4)$$

Herein, since substantially the same characteristics as the bandpass filter shown in formula (2) above are expressed by that arrived at by connecting a low-pass filter and high-pass filter in series, the cut-off frequency LPF$\omega c$ is set to a value larger than the cut-off frequency HPF$\omega c$. In addition, similarly to setting the resonance frequency of the mechanical system within the bandwidth of the bandpass filter in Example 1, the filter transfer functions $G_{LPF}$ and $G_{HPF}$ are set so that the above-mentioned resonance frequency is included in the bandwidth between the cut-off frequencies HPFωc and LPFωc thereof.

Figure 7:
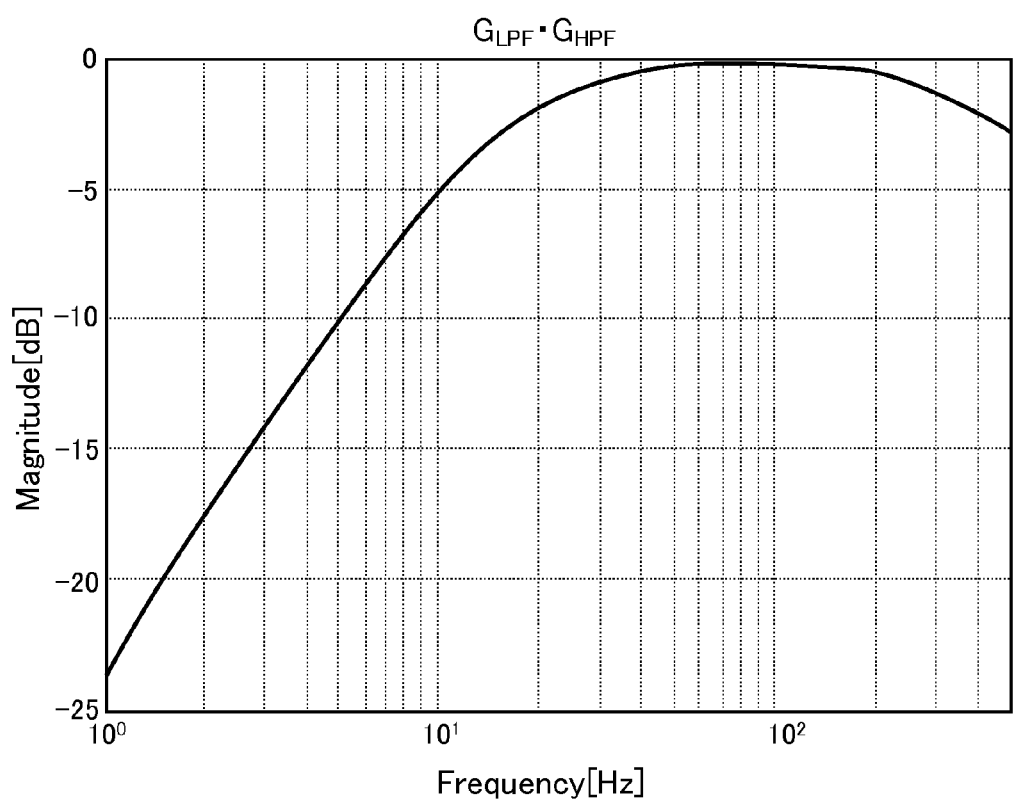
FIG. 7 is a graph showing the frequency characteristics of transfer functions $G_{LPF}$ and $G_{HPF}$ of Example 2.

FIG. 7 is a graph showing the frequency characteristics of the filter transfer functions $G_{LPF}$, and $G_{HPF}$. FIG. 7 shows an example of the filter transfer functions $G_{LPF}$ and $G_{HPF}$ set under the assumption that there is a resonance point of the mechanical system in the vicinity of 100 Hz, similarly to FIG. 4.

In addition to the effect of above-mentioned (1), there is the following effect according to the present example.

(3) As is clear when comparing between the frequency characteristics of the filter transfer functions $G_{LPF}$ and $G_{HPF}$ shown in FIG. 7 and the frequency characteristics of the filter transfer functions $G_{LPF}$ and $G_{HPF}$ shown in FIG. 4, configuring by connecting the low-pass filter and high-pass filter in series tends to set the bandwidth of the peak gain vicinity wider. For this reason, when compared with the above-mentioned Example 1, it is possible to improve the degree of freedom in design of the shaft-torque-detection-compensation unit.

MODIFIED EXAMPLE OF EXAMPLE 2

Next, a modified example of Example 2 will be explained in detail by referencing the drawings.

Figure 8:
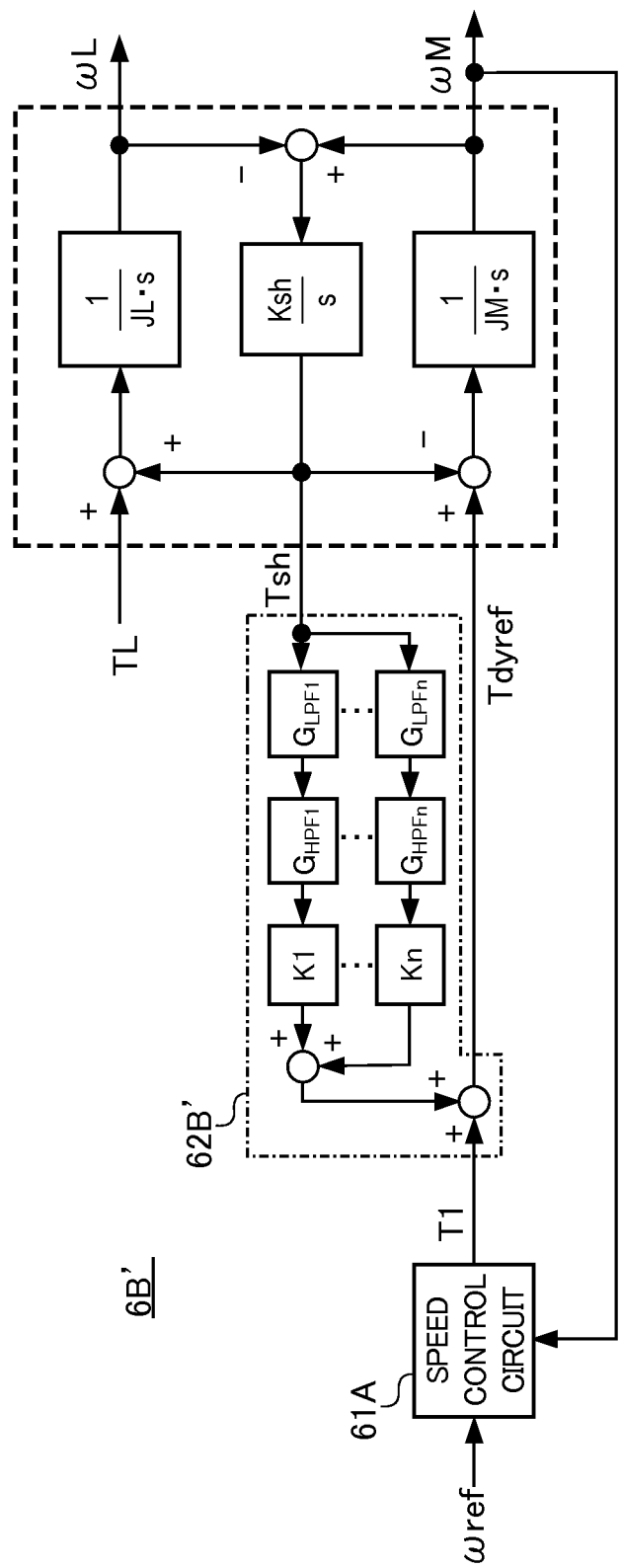
FIG. 8 is a block diagram showing the entirety of a control system of a modified example of Example 2.

FIG. 8 is a block diagram showing the entirety of a control system to which a speed-control device 6B' of the present modified example is applied. Comparing with the above-mentioned Example 2 shown in FIG. 6, the configuration of the shaft-torque-detection-compensation unit 62B' differs.

The shaft-torque-detection-compensation unit 62B' of the present modified example assumes that a plurality of resonance points exist, and is configured by joining a plurality of the filter transfer functions $G_{LPFn}$ and $G_{HPFn}$ set for each resonance frequency and suppression gains Kn in parallel. More specifically the shaft-torque-detection-compensation unit 62B' sets the filter transfer functions $G_{LPFn}$ and $G_{HPFn}$ and suppression gains Kn as explained in the above-mentioned Example 2 for each resonance frequency, and establishes a value summing all of the compensation amounts Tsh_Kn obtained by multiplying the shaft torque meter detection value Tsh by each of the filter transfer functions $G_{LPFn}$ and $G_{HPFn}$ and suppression gains Kn, as the shaft-torque-detection-compensation amount Tsh_K.

Substantially the same effects as the effects of the above-mentioned (1), (2) and (3) are exerted according to the present modified example.

EXAMPLE 3

Next, Example 3 of a speed-control device of the above-mentioned embodiment will be explained while referencing the drawings.

Figure 9:
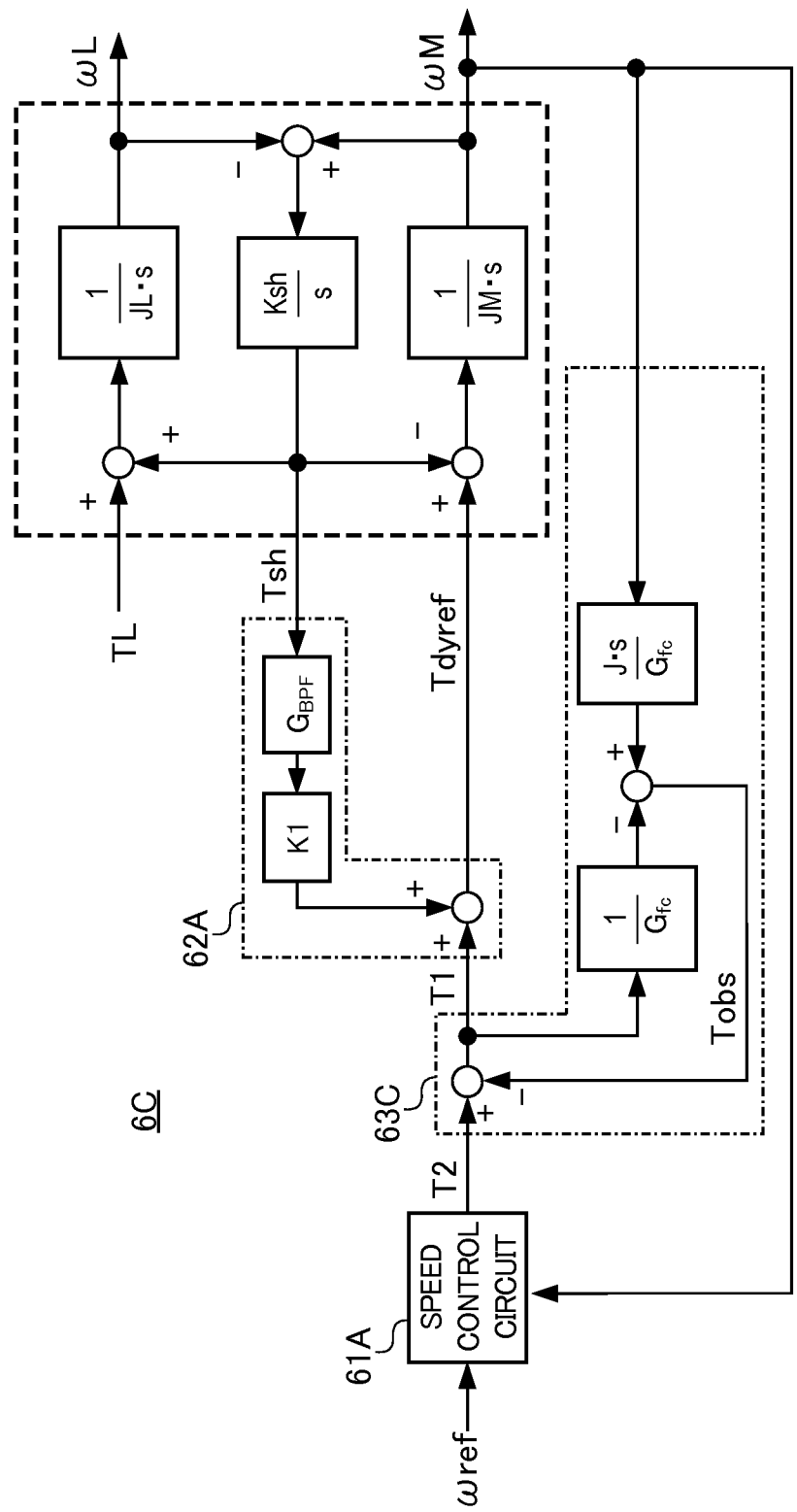
FIG. 9 is a block diagram showing the entirety of a control system of Example 3.

FIG. 9 is a block diagram showing the entirety of a control system to which a speed-control device 6C of the present example is applied. The speed-control device 6C of the present example differs in the aspect of further including a disturbance observer compensation unit 63C, compared to the above-mentioned Example 1.

In the present example, a value arrived at by subtracting a disturbance observer Tobs calculated by the disturbance observer compensation unit 63C, and then further adding the shaft-torque-detection-compensation amount Tsh_K calculated by the shaft-torque-detection-compensation unit 62A, to a torque-current-command value T1 calculated by the speed-control-circuit 61A, becomes a final torque-current-command value Tdyref.

The disturbance observer compensation unit 63C calculates the disturbance observer Tobs according to formula (6) below, based on the dynamometer angular velocity ωM and the torque-current-command value T1, and subtracts this from the torque-current-command value T1 calculated by the speed-control-circuit 61A, so as to correct the torque-current-command value T2. More specifically, as shown in formula (6) below, the disturbance observer compensation unit 63C establishes, as the disturbance observer Tobs, a value arrived at by calculating an estimated value of disturbance by subtracting the torque-current-command value T1 from a value obtained by multiplying the dynamometer angular velocity ωM by an inverse model transfer function J·s, and then further multiplying the transfer function 1/Gfc(s).

$$Tobs = \frac{(J \cdot \omega M \cdot s) - T1}{Gfc(s)} \quad (6)$$

Herein, the inertia moment J used in the inverse model transfer function J·s establishes an overall inertia moment (J=JM+JL) combining the dynamometer and electric motor.

In order to improve the accuracy of the disturbance observer, for the transfer function 1/Gfc(s), any transfer function with a relative degree of at least 1 having a characteristic of preventing a higher frequency band than a predetermined cut-off frequency is used. In addition, the cut-off frequency of this transfer function 1/Gfc(s) is set lower than the resonance frequency of the above-mentioned mechanical system used in setting of the filter transfer function $G_{PBF}$, in order to avoid interference with the shaft-torque-detection-compensation unit 62A.

In addition to the effect of the above-mentioned (1), the following effect is exerted according to the present example.

(4) in the present example, the disturbance observer compensation unit 63C is further provided, and by correcting the torque-current-command value T2 calculated by the speed-control-circuit 61A with the disturbance observer Tobs calculated based on the dynamometer angular velocity ωM and torque-current-command value T1, the disturbance response improves, whereby more highly-responsive speed control of the dynamometer becomes possible. In addition, with the present example, by combining the disturbance observer compensation unit 63C to use with the shaft-torque-detection-compensation unit 62A set so as to compensate only the resonance frequency band, both cooperate, whereby highly-responsive and stable speed control over the entire frequency band becomes possible.

(5) According to the present example, by calculating the disturbance observer Tobs as an estimated value of disturbance by an inverse model taking consideration of the overall inertia moment J combining the electric motor and dynamometer, and correcting the torque-current-command value T1 with this, the disturbance response is improved, and more highly-responsive speed control of the dynamometer becomes possible. In addition, by multiplying the transfer function 1/Gfc(s) having the above-mentioned such low-pass characteristic, the accuracy of the disturbance observer Tobs can be improved.

Figure 10:
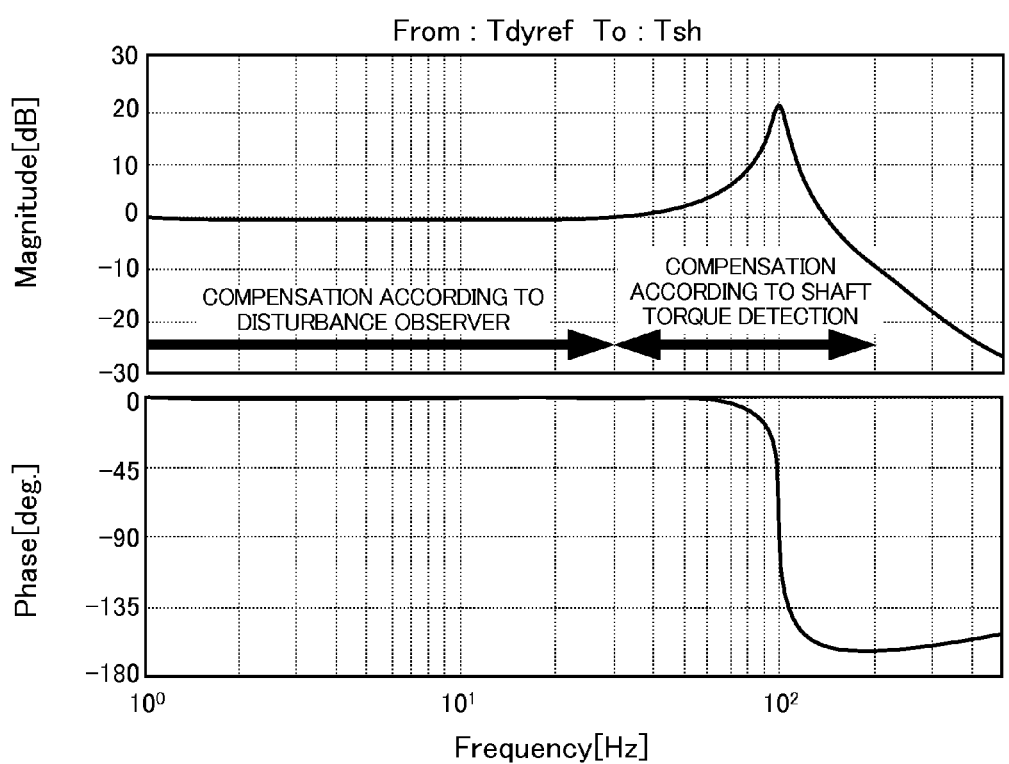
FIG. 10 is a Bode diagram showing the frequency response from a torque-current-command value to a shaft torque meter detection value.

(6) FIG. 10 is a Bode diagram showing the frequency response from a torque-current-command value Tdyref to a shaft torque meter detection value Tsh. As shown in FIG. 10, a resonance point exists in the vicinity of 100 Hz in this mechanical system. Addressing this, with the present example, the bandpass filter $G_{BPF}$ having a bandwidth in the vicinity of the resonance frequency is provided to the shaft-torque-detection-compensation unit 62A, and by making the cut-off frequency of the disturbance observer compensation unit 63C lower than the above-mentioned resonance frequency, as shown schematically by the bold arrows in FIG. 10, it is configured so as to compensate with the disturbance observer compensation unit 63C on the low frequency side, and configured to compensate with the shaft-torque-detection-compensation unit 62A on the high frequency side, whereby highly-responsive and stable speed control over the entire frequency range becomes possible by both cooperating.

EXAMPLE 4

Next, Example 4 of a speed-control device of the above-mentioned embodiment will be explained while referencing the drawings.

Figure 11:
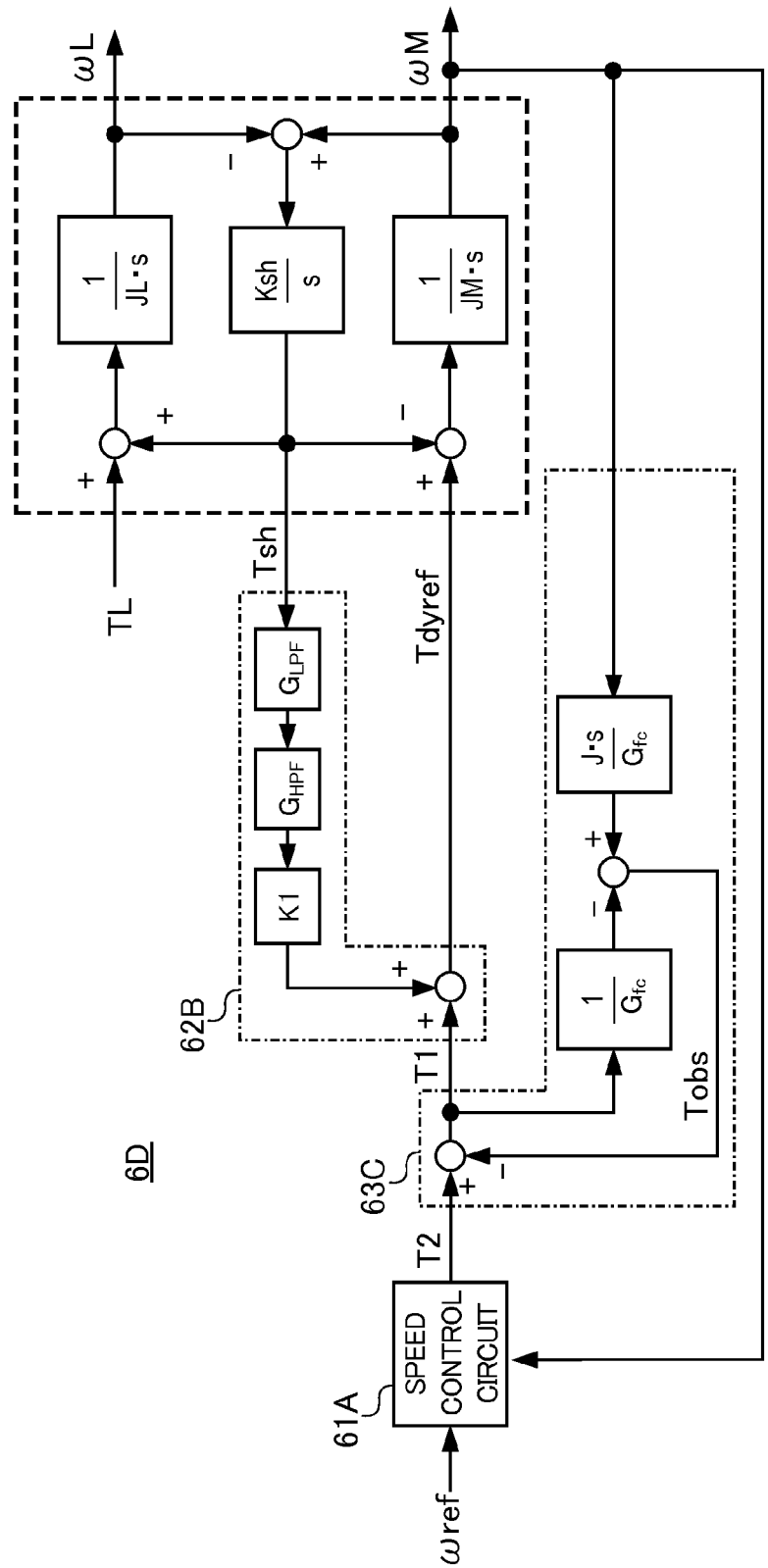
FIG. 11 is a block diagram showing the entirety of a control system of Example 4.

FIG. 11 is a block diagram showing the configuration of a speed-control device 6D of the present example. The speed-control device 6D of the present example differs in the point of further including a disturbance observer compensation unit 63C, compared to the above-mentioned Example 2. It should be noted that the configuration of this disturbance observer compensation unit 63C is the same configuration as that explained in the above-mentioned Example 3, and thus a detailed explanation thereof is omitted.

Substantially the same effects as the effects of the above-mentioned (1), (3), (4), (5) and (6) are exerted according to the present example.

Although an embodiment and examples of the present invention have been explained above, the present invention is not to be limited thereto. For example, in the above-mentioned examples, examples in which the shaft-torque-detection-compensation unit and disturbance observer compensation unit were applied to the speed-control device with the dynamometer angular velocity as a controlled variable are explained; however, the present invention is not to be limited thereto. For example, the same effects can be expected even if applying the same shaft-torque-detection-compensation unit or disturbance observer compensation unit to a position control device having a speed control unit in a minor loop with the rotational position of the dynamometer as the controlled variable.

The invention claimed is:

1. A dynamometer system comprising:
a dynamometer that is connected by a common shaft to a load device;
an inverter that supplies electric power to the dynamometer;
an encoder that detects a rotational position or angular velocity of the dynamometer;
a shaft torque meter that detects shaft torque between the load device and the dynamometer; and
a control device that controls the dynamometer based on a detection value of the encoder and a detection value of the shaft torque meter,
wherein the control device includes:
a main control unit that calculates a torque-current-command value to serve as an input to the inverter, based on a command value relative to the detection value of the encoder inputted externally, and the detection value of the encoder;
a shaft-torque-detection-compensation unit that adds a compensation amount obtained by multiplying a filter transfer function and a suppression gain by the detection value of the shaft torque meter, to the torque-current-command value calculated by the main control unit, so as to correct the torque-current-command value; and
a disturbance observer compensation unit that calculates a disturbance observer based on the detection value of the encoder and the torque-current-command value calculated by the main control unit, and subtracts the disturbance observer thus calculated from the torque-current-command value calculated by the main control unit, so as to correct the torque-current-command value,
wherein the filter transfer function of the shaft-torque-detection-compensation unit is set with only a resonance frequency of a mechanical system consisting of the load device and the dynamometer and a vicinity thereof as a passband, and
wherein the disturbance observer compensation unit has a characteristic of blocking a frequency band higher than a cutoff frequency which is set to be lower than the resonance frequency.

2. The dynamometer system according to claim 1, wherein the disturbance observer compensation unit calculates a disturbance observer Tobs by way of the formula below, wherein J is an overall inertia moment combining the dynamometer and the load device, ωM is the detection value of the encoder, T1 is the torque-current-command value calculated by the main control unit, s is a Laplace operator, 1/Gfc(s) is any transfer function having a relative degree of at least one dimension and having a characteristic of blocking a frequency band higher than the cut-off frequency $$Tobs = \frac{(J \cdot \omega M \cdot s) - T1}{Gfc(s)}.$$

3. The dynamometer system according to claim 2, wherein the cut-off frequency is a cut-off frequency of the transfer function 1/Gfc(s).

4. The dynamometer system according to claim 3, wherein the filter transfer function of the shaft-torque-detection-compensation unit is a band-pass filter set so that the resonance frequency of the mechanical system is included in the bandwidth thereof.

5. The dynamometer system according to claim 3, wherein the filter transfer function of the shaft-torque-detection-compensation unit is configured by connecting a high-pass filter having a cut-off frequency lower than the resonance frequency in series to a low-pass filter having a cut-off frequency higher than the resonance frequency.

6. The dynamometer system according to claim 4,
wherein the shaft-torque-detection-compensation unit is configured by joining in parallel a plurality of filter transfer functions set for each of the resonance frequencies and a suppression gain thereof, for a plurality of resonance frequencies of the mechanical system.

7. The dynamometer system according to claim 5,
wherein the shaft-torque-detection-compensation unit is configured by joining in parallel a plurality of filter transfer functions set for each of the resonance frequencies and a suppression gain thereof, for a plurality of resonance frequencies of the mechanical system.

* * * * *